US00PP31324P2

(12) United States Plant Patent
Smith

(10) Patent No.: US PP31,324 P2
(45) Date of Patent: Jan. 7, 2020

(54) ***CHRYSANTHEMUM* PLANT NAMED 'CIFZ0068'**

(50) Latin Name: ***Chrysanthemum* x *morifolium***
Varietal Denomination: CIFZ0068

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/350,949

(22) Filed: Feb. 4, 2019

(51) Int. Cl.
*A01H 5/02* (2018.01)

(52) U.S. Cl.
USPC ..... Plt./294

(58) Field of Classification Search
USPC ..... Plt./294, 288
CPC ..... A01H 5/02
See application file for complete search history.

*Primary Examiner* — Annette H Para
(74) *Attorney, Agent, or Firm* — Dale Skalla

(57) ABSTRACT

A new garden type *Chrysanthemum* plant named 'CIFZ0068' particularly distinguished by its medium size plant with round mound plant habit, a medium-small (1.75 inch) size flower, white flower color and a natural season response in early-mid September.

1 Drawing Sheet

Figure 1:
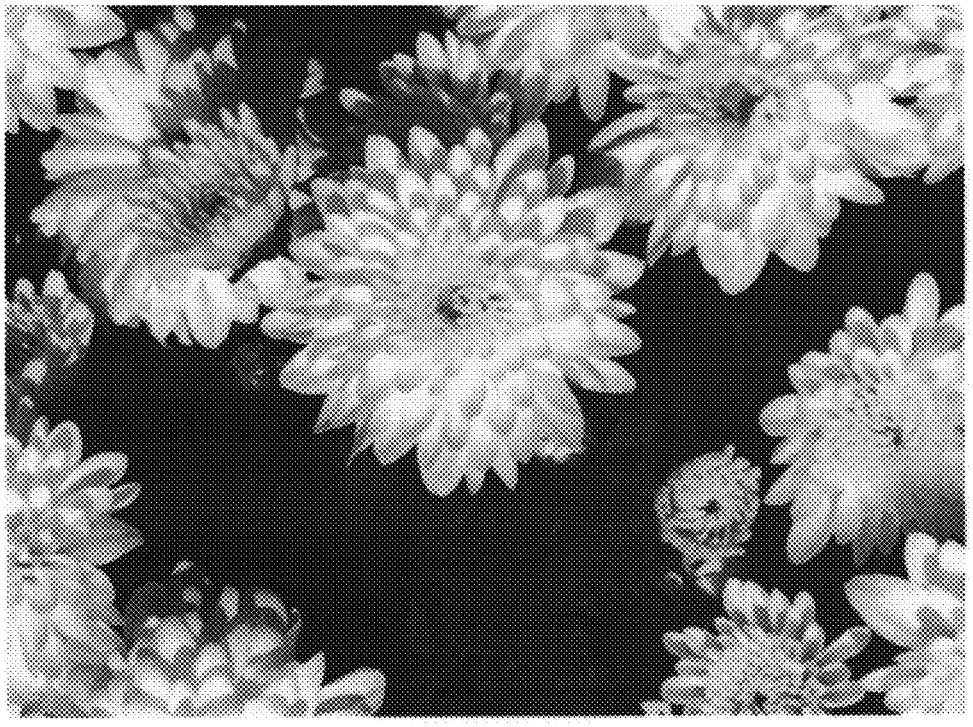

Latin name of the genus and species of the plant claimed: *Chrysanthemum* x *morifolium*.

Varietal denomination: 'CIFZ0068'.

BACKGROUND OF THE NEW PLANT

The present invention comprises a new *Chrysanthemum*, botanically known as *Chrysanthemum* x *morifolium*, and hereinafter referred to by the variety name 'CIFZ0068'.

'CIFZ0068' is a product of a planned breeding program. The new cultivar has medium size plant with round mound plant habit, a medium-small (1.75 inch) size flower, white flower color and a natural season response in early-mid September 'CIFZ0068' originated from a cross made in February 2013 in Enkhuizen, The Netherlands. Seeds were sown in June 2013 in Gilroy, Calif. and 'CIFZ0068' was selected from the resulting population on October 11 in Monroeville, N.J.

The female parent was the unnamed seedling '09-M188'. When compared to the female parent, 'CIFZ0068' has:

A similar flower size and flower type but flower color is white not yellowy-bronze like the female parent.
A one week faster blackcloth response and five week faster natural season response (four weeks faster in the south) than the female parent.
A similar plant size and plant habit as the female parent.

The male parent was the unnamed seedling '02-M490'. When compared to the male parent, 'CIFZ0068' has:

A similar flower size and color but less disc florets than the male parent.
A one week slower blackcloth response and a one week slower natural season response than the male parent.
A larger overall plant size and rounder plant habit than the male parent.

The first act of asexual reproduction of 'CIFZ0068' was accomplished when vegetative cuttings were propagated from the initial selection in January 2014 in Mebane, N.C.

BRIEF SUMMARY OF INVENTION

Horticultural examination of plants grown from cuttings of the plant initiated in January 2014 and continuing thereafter, has demonstrated that the combination of characteristics as herein disclosed for 'CIFZ0068' are firmly fixed and are retained through successive generations of asexual reproduction.

'CIFZ0068' has not been observed under all possible environmental conditions. The phenotype may vary significantly with variations in environment such as temperature, light intensity and day length.

A Plant Breeder's Right for this cultivar has not yet been applied for. 'CIFZ0068' has not been made publicly available prior to the effective filing date of this application, notwithstanding any disclosure that may have been made less than one year prior to the effective filing date of this application by the inventor or another who obtained 'CIFZ0068' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0068' with colors being as true as possible with an illustration of this type. The photographic drawing shows in FIG. 1 a close view of flower of the new variety and in FIG. 2 a flowering plant from an outdoor trial.

Figure 2:
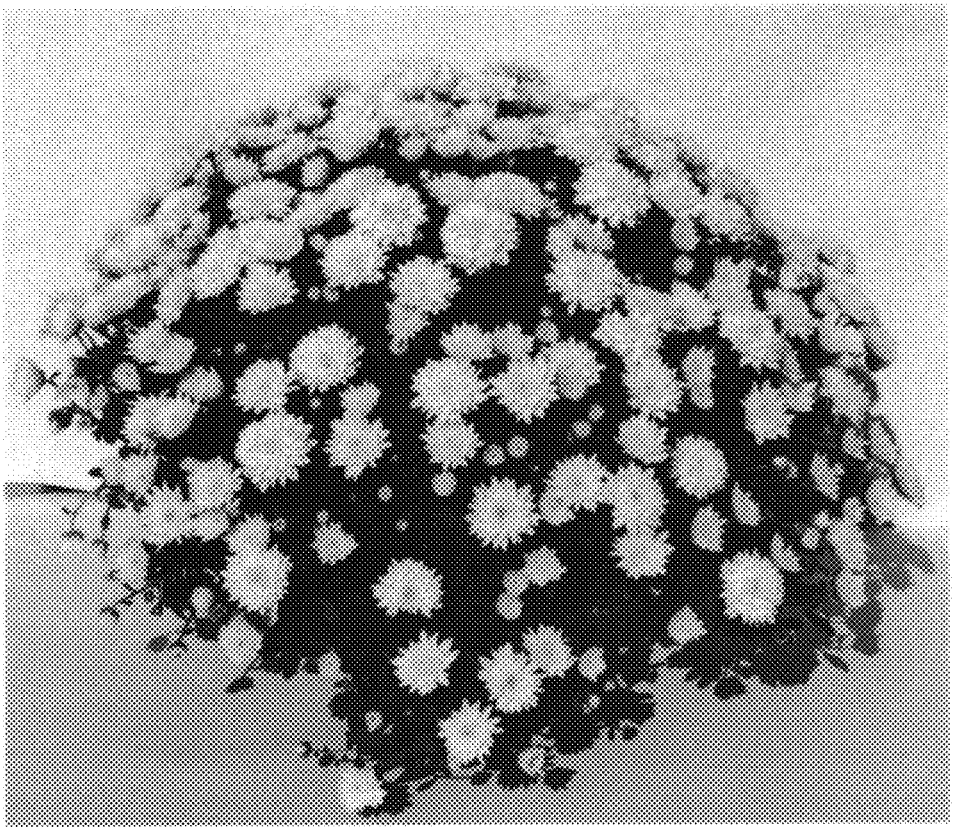

The aforementioned photographs: FIG. 1, as well as FIG. 2, were taken in August 2018 both showing a plant from the same blackcloth indoor trial in Gilroy, Calif.

These plants were about 10 weeks of age. One rooted cutting per pot had been planted in a one gallon pot, not pinched in week 24, and black clothed from week 25. Plants started flowering in August.

DETAILED BOTANICAL DESCRIPTION

The measurements were taken in Gilroy, Calif. in August 2018 on the plants from the aforementioned trial.

Color references are made to The Royal Horticultural Society Colour Chart (R.H.S.) 2015.

TABLE 1

DIFFERENCES BETWEEN THE NEW VARIETY 'CIFZ0068' AND TWO MOST SIMILAR VARIETIES:

| | 'CIFZ0068' | 'CIFZ0029', U.S. Plant Pat. No. 23,874 |
|---|---|---|
| Flowering response (blackcloth): | One week slower | One week faster |
| Flowering response (natural): | Similar | Similar |
| Flower color: | Similar | Similar |
| Flower size: | Smaller | Bigger |
| Plants, stems, flexibility: | More sturdy, less splitting plants | Less sturdy, more splitting plants |
| Plant habit or size: | Similar plant size and plant habit | Similar plant size and plant habit |
| | **'CIFZ0068'** | **'Zanmuspen', U.S. Plant Pat. No. 21,205** |
| Flowering response (blackcloth): | Similar | Similar |
| Flowering response (natural): | Similar | Similar |
| shape/size similar | Similar, but more disk florets | Similar, but with less disk florets |
| Flower color: | Similar | Similar |
| Plants, stems, flexibility: | More stiff plant | More soft plant |
| Plant habit or size: | Rounder plant habit, larger plant | Less round plant habit, smaller plant |

Plant:

*Form, growth and habit.*—Herbaceous garden-type, stems upright and outwardly spreading, freely branching, strong and moderately vigorous growth habit.

*Plant height (above soil).*—4-15 cm.

*Plant height (inflorescence included).*—12-25 cm.

*Plant width.*—42-45 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B but whiter.

Foliage:

*Arrangement.*—Alternate.

*Immature leaf, color upper surface.*—RHS 137A.

*Immature leaf, color lower surface.*—RHS 137C.

*Mature leaf, color, upper surface.*—RHS 137A.

*Mature leaf, color lower surface.*—RHS NN137C.

*Length.*—5.2-5.3 cm.

*Width.*—4.5-4.9 cm.

*Shape.*—Ovate, with distinct lobes.

*Base shape.*—Attenuate.

*Apex shape.*—Mucronate.

*Margin.*—5-lobed (palmate), edge dentate.

*Texture, upper surface.*—Bifid hairs.

*Texture, lower surface.*—Bifid hairs.

*Color of veins, upper surface.*—RHS 138B.

*Color of veins, lower surface.*—RHS N138B.

*Pattern of veining.*—Palmate.

*Petiole color.*—RHS 138A.

*Petiole length.*—1.2-1.3 cm.

*Diameter.*—0.3 cm.

*Texture.*—Bifid hairs.

Stem:

*Quantity of main branches per plant.*—6-8.

*Color of stem.*—RHS 138A.

*Length of stem.*—6-8.5 cm.

*Diameter.*—0.5 cm.

*Length of internodes.*—0.8 cm.

*Texture.*—Bifid hairs.

*Color of peduncle.*—RHS 138B.

*Length of peduncle.*—7.2-8.6 cm.

*Peduncle diameter.*—0.3 cm.

*Texture.*—Bifid hairs.

Inflorescence:

*Type.*—Compositae, solitary, decorative type inflorescences borne terminally above foliage, ray and disc florets arranged on a capitulum.

*Quantity of short days to flowering (response time).*—Approximately 5 weeks.

*Natural season flowering.*—Early to mid September.

*Quantity of inflorescences per plant.*—160-180.

*Lastingness of individual blooms on the plant.*—About five weeks from first color.

*Fragrance.*—Slightly spicy.

Bud (when showing color):

*Color.*—RHS 158C.

*Length.*—1.6 cm.

*Width.*—1.9 cm.

*Shape.*—Oblate.

Immature inflorescence:

*Diameter.*—2.5-3.5 cm.

*Color of ray florets, upper surface.*—RHS 158D.

*Color of ray florets, lower surface.*—RHS 61A, overlain with RHS 158D.

Mature inflorescence:

*Diameter.*—4.8 cm.

*Depth.*—1.2 cm.

*Total diameter of disc.*—0.8 cm.

*Receptacle color.*—RHS 139A.

*Receptacle height.*—0.9-1.0 cm.

*Receptacle diameter.*—0.3 cm.

Ray florets:

*Average quantity of florets.*—Between 130 and 140 in several whorls.

*Color of florets, upper surface (abaxial).*—RHS 155D.

*Color inner surface (adaxial).*—RHS 155D.

*Length.*—2.8 cm.

*Width/diameter.*—0.6 cm.

*Shape.*—Elliptical.

*Apex shape.*—Most obtuse and dentate.

*Base shape.*—Tube.

*Margin.*—Entire, small incisions may occur at the tip.

*Texture, upper surface.*—Papillate.

*Lower surface.*—Papillate.

Disc florets: 50-60.

*Width.*—0.1 cm.

*Length.*—0.4 cm.

*Color.*—RHS 61B at apex, RHS N144D at base.

Phyllaries:

*Quantity.*—10-20.

*Color, upper surface.*—RHS 137A.

*Color, lower surface.*—RHS 137A.

*Length.*—0.7-0.8 cm.

*Width.*—0.2 cm.

*Shape.*—Lanceolate.

*Apex shape.*—Acute.

*Base.*—Fused.

*Margins.*—Entire.

*Texture, upper surface.*—Glabrous.

*Texture, lower surface.*—Canescent.

Reproductive organs:

*Pistil.*—One.

*Length.*—0.3-0.5 cm.

*Style color.*—RHS 150B.

*Style length.*—0.2-0.3 cm.

*Stigma color.*—RHS 13B.

*Stigma shape.*—Bi-parted.

*Ovary color.*—RHS 145C.

*Ovary length.*—0.15 cm.

*Ovary width.*—0.1 cm.

Androecium:

*Stamens.*—1, found on only disc florets.

*Color of filaments.*—RHS 9C.

*Length filaments.*—0.2 cm.

*Anther color.*—RHS 13B.

*Anther length.*—0.2 cm.

*Anther shape.*—Oval to club shaped.

*Color of pollen.*—RHS 13B.

*Pollen amount.*—Moderate.

*Fertility/seed set.*—Fertile as male parent.

*Disease/pest resistance.*—Has not been determined to date.

What is claimed is:

1. A new and distinct variety of *Chrysanthemum* plant named 'CIFZ0068' substantially as illustrated and described herein.

* * * * *